United States Patent [19]

Dill, Jr. et al.

[11] Patent Number: 4,666,509
[45] Date of Patent: May 19, 1987

[54] HERBICIDE ANTIDOTES FOR COTTON CROPS

[75] Inventors: Gerald M. Dill, Jr., Ballwin, Mo.; Georgina M. Malloy Werner, Raleigh, N.C.

[73] Assignee: Union Carbide Corporation, Danbury, Conn.

[21] Appl. No.: 683,426

[22] Filed: Dec. 19, 1984

[51] Int. Cl.$^4$ ............................................. A01N 25/32
[52] U.S. Cl. ............................................. 71/93; 71/120
[58] Field of Search ................................... 71/93, 120

[56] References Cited

U.S. PATENT DOCUMENTS 2,891,855  6/1959  Gysin et al. ............................ 71/2.5
4,230,482  10/1980  Peterson ................................. 71/93
4,231,785  11/1980  Peterson ................................. 71/93
4,353,733  10/1980  Raven et al. ........................... 71/93

FOREIGN PATENT DOCUMENTS 2200325  7/1973  Fed. Rep. of Germany .
157525  12/1975  Japan .
 19937  2/1979  Japan .
720072  1/1972  South Africa .
1324406  7/1973  United Kingdom .

OTHER PUBLICATIONS

Showa Denko K.K. Technical Information Bulletin, K-3185 Herbicide, Form 85-11/77S, pp. 1-6.
Showa Denko K.K. Technical Information Bulletin, Stacker (Code No. K-1441), Selective Herbicide, Form 41-21/74F, pp. 1-8.

Primary Examiner—Catherine L. Mills
Attorney, Agent, or Firm—Gerald L. Coon

[57] ABSTRACT

This invention relates to novel herbicidal compositions containing (i) a herbicidally effective amount of a herbicidal compound selected from atrazine [2-chloro-4-(ethylamino)-6-(isopropylamino)S-triazine] and cyanazine [2-chloro-4-(1-cyano-1-methylethylamino)-6-ethylamino-S-triazine] and (ii) an antidotally effective amount of an antidotal compound having the formula

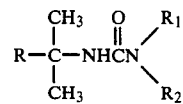

wherein R, $R_1$ and $R_2$ are as defined herein. This invention also relates to methods for protecting cotton plants from injury due to conventional herbicides and for the selective control of undesirable vegetation in cotton crops by application of the novel herbicidal compositions.

12 Claims, No Drawings

HERBICIDE ANTIDOTES FOR COTTON CROPS

BRIEF SUMMARY OF THE INVENTION

1. Technical Field

This invention relates to novel herbicidal compositions which act to protect cotton plants from damage caused by conventional herbicides without significantly reducing the effectiveness of such herbicides with respect to controlling undesirable weeds. This invention also relates to methods for protecting cotton plants from injury due to conventional herbicides and for the selective control of undesirable vegetation in cotton crops by application of the novel herbicidal compositions.

2. Background of the Invention

It is oftentimes difficult to find herbicidal compositions which exhibit desirable selectivity, that is, which will control undesirable weeds but which will not damage the desirable crop plant. In many instances, antidotes or safeners have been found which, when applied in combination with a particular herbicide, act to protect the desirable crop plant from damage caused by the herbicide but which do not adversely affect the action of the herbicide on undesirable weeds. See, for example, U.S. Pat. No. 4,230,482 and U.S. Pat. No. 4,231,785.

In particular, atrazine [2-chloro-4-(ethylamino)-6-(isopropylamino)-S-triazine] and cyanazine [2-chloro-4-(1-cyano-1-methylethylamino)-6-ethylamino-S-triazine] are commercially available herbicidal compounds which are widely used as selective herbicides for the control of annual grass and broadleaf weeds in various crop plants. However, atrazine and cyanazine are generally unsatisfactory for controlling undesirable weeds in cotton crops. Atrazine and cyanazine each exhibit undesirable toxicity with respect to cotton plants at the dosages required to control undesirable weeds.

Accordingly, one or more of the following objects will be achieved by the practice of this invention. It is an object of this invention to provide novel herbicidal compositions which act to protect cotton plants from damage caused by conventional herbicides without significantly reducing the effectiveness of such herbicides with respect to controlling undesirable weeds. Another object of this invention is to provide a method for protecting cotton plants from injury due to conventional herbicides by application of the novel herbicidal compositions. A further object of this invention is to provide a method for the selective control of undesirable vegetation in cotton crops by application of the novel herbicidal compositions. These and other objects will readily become apparent to those skilled in the art in light of the teachings herein set forth.

DISCLOSURE OF THE INVENTION

This invention relates to novel herbicidal compositions containing (i) a herbicidally effective amount of a herbicidal compound selected from atrazine [2-chloro-4-(ethylamino)-6-(isopropylamino)-S-triazine] and cyanazine [2-chloro-4-(1-cyano-1-methylethylamino)-6-ethylamino-S-triazine] and (ii) an antidotally effective amount of an antidotal compound having the formula

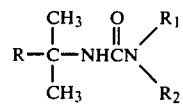

wherein R, $R_1$ and $R_2$ are as hereinafter described.

This invention also relates to a method of protecting cotton plants from injury due to a herbicidal compound selected from atrazine [2-chloro-4-(ethylamino)-6-(isopropylamino)-S-triazine] and cyanazine [2-chloro-4-(1-cyano-1-methylethylamino)-6-ethylamino-S-triazine] which comprises combining application of a herbicidally effective amount of said herbicidal compound to the locus to be treated with application of an antidotally effective amount of an antidotal compound having the formula

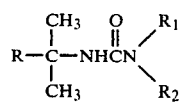

wherein R, $R_1$ and $R_2$ are as hereinafter described, to the locus to be treated or to the cotton seed.

This invention further relates to a method for the selective control of undesirable vegetation in cotton crops by application of the novel herbicidal compositions.

DETAILED DESCRIPTION

As indicated above, the novel herbicidal compositions of this invention act to protect cotton plants from damage caused by conventional herbicides without significantly reducing the effectiveness of such herbicides with respect to controlling undesirable weeds.

The novel herbicidal compositions of this invention are defined as containing (i) a herbicidally effective amount of a herbicidal compound selected from atrazine [2-chloro-4-(ethylamino)-6-(isopropylamino)-S-triazine] and cyanazine [2-chloro-4-(1-cyano-1-methylethylamino)-6-ethylamino-S-triazine] and (ii) an antidotally effective amount of an antidotal compound having the formula

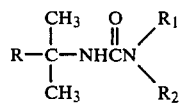

wherein:

R is unsubstituted phenyl or $C_{1-4}$ alkyl substituted phenyl;

$R_1$ is unsubstituted or substituted phenyl wherein the permissible substituents are one or more $C_{1-4}$ alkyl, alkoxy, polyhaloalkyl, aryl, halo or nitro which may be the same or different; and $R_2$ is $C_{1-4}$ alkyl or alkoxy.

The herbicidal component of the compositions of this invention includes either atrazine [2-chloro-4-(ethylamino)-6-(isopropylamino)-S-triazine] or cyanazine [2-chloro-4-(1-cyano-1-methylethylamino)-6-ethylamino-S-triazine]. Atrazine is commercially available from Ciba-Geigy Corporation, Ardsley, N.Y., as AATREX ® Herbicide. Cyanazine is commercially available from Shell Oil Company, Houston, Tex. as BLADEX ® Herbicide.

The antidotal component of the compositions of this invention includes dimethylbenzyl phenyl urea compounds illustrated by the formula hereinabove. Suitable antidotal compounds which serve to protect the cotton crops from damage caused by the herbicides described herein, while not adversely affecting the action of the herbicide in controlling undesirable weeds, includes for example 1-(alpha, alpha-dimethylbenzyl)-3-methyl-3-phenyl urea, 1-(alpha, alpha-dimethylbenzyl)-3-methoxy-3-phenyl urea and the like. The antidotal compound 1-(alpha, alpha-dimethylbenzyl)-3-methyl-3-phenyl urea is commercially available from Showa Denko K.K., Tokyo, Japan, as STACKER® K-1441. The antidotal compound 1-(alpha, alpha-dimethylbenzyl)-3-methyl-3-phenyl urea is available from Showa Kenko K.K., Tokyo, Japan as K-3185.

Other dimethylbenzyl phenyl urea compounds which may be suitable as antidotal compounds in the herbicidal compositions of this invention include the following:

1-(alpha, alpha-dimethylbenzyl)-3-methyl-3-(2,4-dimethylphenyl) urea;
1-(alpha, alpha-dimethylbenzyl)-3-methoxy-3-(3-methoxyphenyl) urea;
1-(alpha, alpha-dimethylbenzyl)-3-methyl-3-(3-trifluoromethylphenyl) urea;
1-(alpha, alpha-dimethylbenzyl)-3-methyl-3-(diphenyl) urea;
1-(alpha, alpha-dimethylbenzyl)-3-methyl-3-(3-nitrophenyl) urea;
1-(alpha, alpha-dimethylbenzyl)-3-methyl-3-(2-chlorophenyl) urea;
3-(2-p-tolylisopropyl)-1-methyl-1-(3-methylphenyl) urea.

Dimethylbenzyl phenyl urea compounds and the preparation thereof are described in the literature, for example, in Japanese Kokai JP No. 50/157525 [75/157525], published Dec. 19, 1975, and German Patent Application DE No. 2,200,325, published July 12, 1973.

For instance, suitable dimethylbenzyl phenyl urea compounds may be prepared according to the procedure represented by the following reaction scheme:

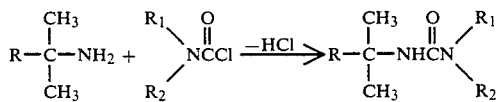

wherein R, $R_1$ and $R_2$ are as defined hereinabove. This procedure is described in South African Patent Application ZA No. 72/72, published Aug. 22, 1972.

Another procedure for preparing suitable dimethylbenzyl phenyl urea compounds is illustrated by the following reaction scheme:

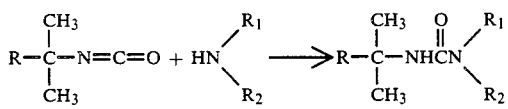

wherein R, $R_1$ and $R_2$ are as defined hereinabove. The reaction can be carried out at about ambient temperature in the presence of alcohols, phenols, carboxylic acids, acetylacetones or water. This procedure is described in Japanese Kokai JP No. 54/19937 [79/19937], published Feb. 15, 1979.

A number of methods are available for combining application of the herbicidal compounds and antidotal compounds described herein. The herbicidal compound and antidotal compound may be applied by preemergence application (applied to the soil after planting but before cotton plants emerge), by preemergence incorporated application (applied to the soil and exposed cotton seeds in furrow prior to completion of planting), by preplant incorporated application (applied to the soil and mixed into the soil before planting), by seed application (applied to cotton seed prior to planting), or by combinations of the above applications. The herbicidal compounds and antidotal compounds may be applied either simulataneously or sequentially, with the antidotal compound application either preceeding or following the herbicidal compound application. The herbicidal compounds and antidotal compounds may be formulated separately and applied separately or formulated together in the proper weight ratio and applied together as a tank mix.

The ratio of antidotal compound to herbicidal compound used in the compositions of this invention will vary, depending upon the specific antidotal compound and herbicidal compound used and on the method of application used. The cotton species and cultural practices may also have an effect. For example, when the antidotal compound is applied as a seed coating (seed application), it may be applied at a rate of about 0.1 percent to about 0.5 percent of the seed weight. When the cotton seeds are planted at from about 10 kg/ha to about 150 kg/ha, the antidotal compound would be distributed at from about 0.01 kg/ha to about 0.75 kg/ha. In preemergence applications and preplant incorporated applications, the antidotal compound may be supplied at about 0.1 kg/ha to about 10 kg/ha. Similar rates may be used for in-the-row treatments (preemergence incorporated applications); however, since only the furrow is treated, the lower per hectare rate would be diminished to as low as about 0.01 kg/ha, depending upon the row spacing. Since the herbicidal compounds may be used at rates of about 0.001 kg/ha to about 2 kg/ha, the ratio of antidotal compound to herbicidal compound may vary between about 0.005:1 and 10,000:1. One skilled in the art could determine the proper ratio to use in a given situation.

The herbicidal compositions of this invention contain a herbicidal compound and an antidotal compound (active ingredients) and will usually contain a carrier and/or diluent, either liquid or solid. Suitable liquid diluents or carriers include water, acetone or other liquid carriers. Suitable solid carriers include appropriately divided clay, talc, bentonite, diatomaceous earth, fullers earth, and the like, which can be prepared as wettable powders or dust or granulated compositions. The required amount of the herbicidal compositions contemplated herein may be applied per acre treated in from about 0.25 gallons to 200 gallons or more of liquid carrier and/or diluent or in from about 5 to about 500 pounds of inert solid carrier and/or diluent.

The herbicidal compositions of this invention have a high margin of safety and selectivity in that when used in sufficient amount to control undesirable weeds they do not injure the desirable cotton plants. It will be appreciated that the herbicidal compositions contemplated herein can also be used in combination with other biologically active compounds.

Although this invention has been described with respect to a number of details, it is not intended that this invention should be limited thereby. The examples which follow one intended solely to illustrate the embodiments of this invention which to date have been determined and are not intended in any way to limit the scope and intent of this invention.

The herbicidal compositions used in the examples below were applied to the locus to be treated according to the following procedures:

Preemergence application: the herbicidal compositions or herbicidal compounds or antidotal compounds dissolved in acetone were applied to the soil surface in which seeds had been planted prior to emergence of the seeds at an application rate of 100 gallons per acre using a single-nozzle hand held sprayer to give the indicated amounts of herbicidal compound and/or antidotal compound in the examples.

Preemergence incorporated application: the herbicidal compositions or herbicidal compounds or antidotal compounds dissolved in acetone were applied to the soil surface and to exposed seeds in furrow prior to completion of planting at an application rate of 100 gallons per acre using a single-nozzle hand held sprayer to give the indicated amounts of herbicidal compound and/or antidotal compound in the examples. The seeds and soil surface were covered by a thin layer of sand.

Preplant incorporated application: the herbicidal compositions or herbicidal compounds or antidotal compounds dissolved in acetone were applied to the soil and mixed into the soil before planting at an application rate of 100 gallons per acre using single-nozzle hand held sprayer to give the indicated amounts of herbicidal compound and/or antidotal compound in the examples. If a sequential preemergence application was applied, it was applied to the soil surface after planting.

Seed application: seeds were soaked in either a 0.5%, 1.0%, 5.0% or 10.0% solution of the antidotal compound in dichloromethane. The seeds were allowed to soak for 30 minutes to 120 minutes depending upon the length of treatment desired and thereafter dried and stored in airtight containers until used. If a sequential preemergence application was applied, it was applied to the soil surface after planting.

Postemergence application: the herbicidal compositions or herbicidal compounds or antidotal compounds dissolved in acetone were applied to seedlings as the first true leaf was beginning to expand or at the two leaf stage at an application rate of 120 gallons per acre using a single-nozzle hand held sprayer to give the indicated amounts of herbicidal compound and/or antidotal compound in the examples.

In certain of the examples below, herbicidal activity was determined by visual observation of the particular plant species tested with the observations reported as the standard mean of 3 replications based on a scale of 0% (no injury) to 100% (complete necrosis). The observations considered both growth inhibition and necrosis which were correlated to arrive at the particular percentage given in the tables.

As used in the examples and comparative examples hereinafter, the following terms have the designated meanings:

| | |
|---|---|
| Herbicidal Compound I | 2-Chloro-4-(ethylamino)-6-(isopropylamino)-S—triazine, also known as Atrazine, having the formula $$\text{CH}_3\text{—HCHN—} \underset{\substack{N \\ \\ N}}{\overset{\substack{Cl \\ \\ N}}{\bigtriangleup}} \text{—NHC}_2\text{H}_6$$

and commercially available from Ciba-Geigy Corporation, Ardsley, New York, as AATREX ®. |
| Herbicidal Compound II | 2-Chloro-4-(1-cyano-1-methylethylamino)-6-ethylamino-S—triazine, also known as Cyanazine, having the formula $$\text{C}_2\text{H}_5\text{HN—} \underset{\substack{N \\ \\ N}}{\overset{\substack{Cl \\ \\ N}}{\bigtriangleup}} \text{—NH—C(CH}_3\text{)}_2\text{—C≡N}$$

and commercially available from Shell Oil Company, Houston, Texas, as BLADEX ®. |
| Herbicidal Compound III | 2,4-Bis-(isopropylamino)-6-(methylthio)-S—triazine, also known as Prometryn, having the formula $$(\text{CH}_3)_2\text{CHNH—} \underset{\substack{N \\ \\ N}}{\overset{\substack{S—CH}_3 \\ \\ N}}{\bigtriangleup} \text{—NHCH(CH}_3)_2$$

and commercially available from Ciba-Geigy Corporation, Ardsley, New York, as CAPAROL ®. |
| Herbicidal Compound IV | 2-Chloro-4,6-bis-(isopropylamino)-S—triazine, also known as Propazine, having the formula $$(\text{CH}_3)_2\text{CHNH—} \underset{\substack{N \\ \\ N}}{\overset{\substack{Cl \\ \\ N}}{\bigtriangleup}} \text{—NHCH(CH}_3)_2$$

and commercially available from Ciba-Geigy Corporation, Ardsley, New York, as MILOGARD ®. |
| Herbicidal Compound V | 2-Chloro-4,6-bis-(ethylamino)-S—triazine, also known as Simazine, having the formula |

|  |  |
|---|---|
| | 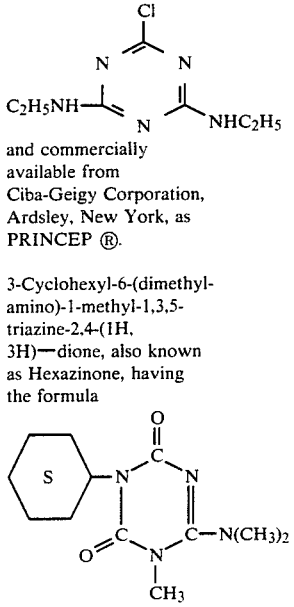and commercially available from Ciba-Geigy Corporation, Ardsley, New York, as PRINCEP ®. |
| Herbicidal Compound VI | 3-Cyclohexyl-6-(dimethyl-amino)-1-methyl-1,3,5-triazine-2,4-(1H,3H)—dione, also known as Hexazinone, having the formula 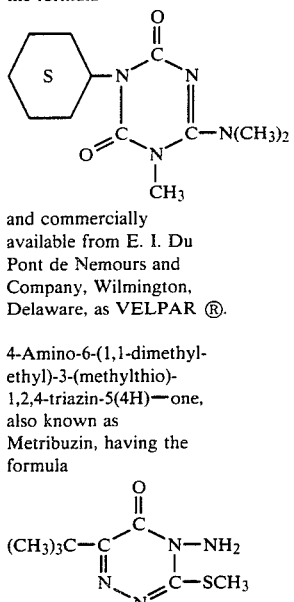and commercially available from E. I. Du Pont de Nemours and Company, Wilmington, Delaware, as VELPAR ®. |
| Herbicidal Compound VII | 4-Amino-6-(1,1-dimethyl-ethyl)-3-(methylthio)-1,2,4-triazin-5(4H)—one, also known as Metribuzin, having the formula 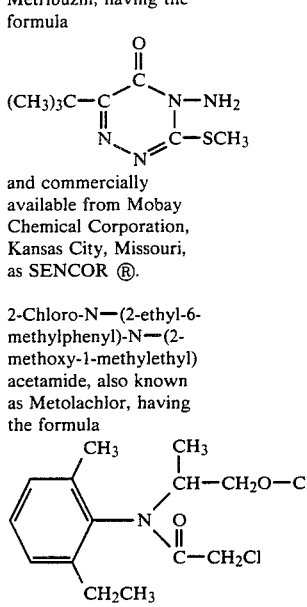and commercially available from Mobay Chemical Corporation, Kansas City, Missouri, as SENCOR ®. |
| Herbicidal Compound VIII | 2-Chloro-N—(2-ethyl-6-methylphenyl)-N—(2-methoxy-1-methylethyl) acetamide, also known as Metolachlor, having the formula 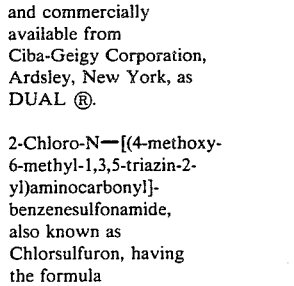and commercially available from Ciba-Geigy Corporation, Ardsley, New York, as DUAL ®. |
| Herbicidal Compound IX | 2-Chloro-N—[(4-methoxy-6-methyl-1,3,5-triazin-2-yl)aminocarbonyl]-benzenesulfonamide, also known as Chlorsulfuron, having the formula 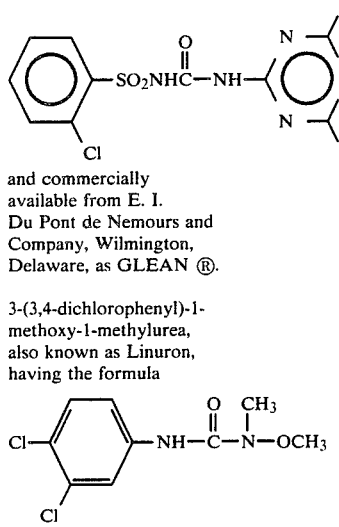and commercially available from E. I. Du Pont de Nemours and Company, Wilmington, Delaware, as GLEAN ®. |
| Herbicidal Compound X | 3-(3,4-dichlorophenyl)-1-methoxy-1-methylurea, also known as Linuron, having the formula 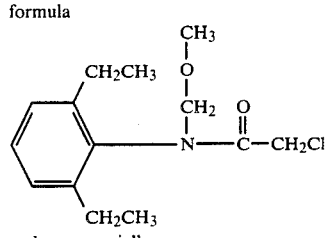and commercially available from E. I. Du Pont de Nemours and Company, Wilmington, Delaware, as LOROX ®. |
| Herbicidal Compound XI | 2-Chloro-N—(2,6-diethyl-phenyl)-N—methoxymethyl-acetamide, also known as Alachlor, having the formula 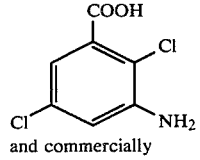and commercially available from Monsanto Company, St. Louis, Missouri, as LASSO ®. |
| Herbicidal Compound XII | 3-Amino-2,5-dichloro benzoic acid, also known as Chloramben, having the formula 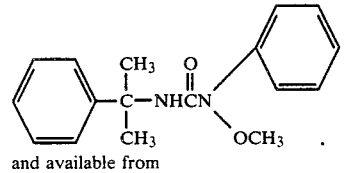and commercially available from Union Carbide Corporation, Danbury, Connecticut, as AMIBEN ®. |
| Antidotal Compound I | 1-(alpha,alpha-Dimethyl-benzyl)-3-methoxy-3-phenyl urea having the formula 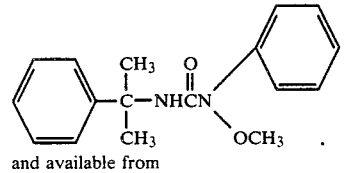and available from Showa Denko K.K., Tokyo, Japan as K-3185. |

| Antidotal Compound II | 1-(alpha,alpha-Dimethyl-benzyl)-3-methyl-3-phenylurea having the formula 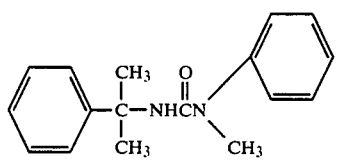 and commercially available from Showa Denko K.K., Tokyo, Japan, as STACKER K-1441. |
|---|---|

9. Killed

EXAMPLES 1-2 AND COMPARATIVE EXAMPLES A-O

The response of the cotton cultivar CAMD-E to the composition mixtures and compounds designated in Table I was determined for preemergence incorporated applications. Approximately 4 weeks after the preemergence incorporated applications, the herbicidal activity of the composition mixtures and compounds was determined by visual observation of the cotton plants. These observations are reported in Table I as the standard mean of 3 replications based on a scale of 0% (no injury) to 100% (complete necrosis).

TABLE I

| Example/ Comparative Example | Treatment | Application Rate (lbs. a1/A) | Weight Ratio (Antidotal Compound/ Herbicidal Compound) | Cotton Injury |
|---|---|---|---|---|
| 1 | Herbicidal Compound I/Antidotal Compound I | 1.50/1.00 | 0.67/1.00 | 7 |
| 2 | Herbicidal Compound II/Antidotal Compound I | 2.00/1.00 | 0.50/1.00 | 10 |
| A | Herbicidal Compound I | 1.50 | — | 100 |
| B | Herbicidal Compound II | 2.00 | — | 100 |
| C | Antidotal Compound I | 1.00 | — | 0 |
| D | Herbicidal Compound XII | 2.00 | — | 3 |
| E | Herbicidal Compound XII/Antidotal Compound I | 2.00/1.00 | 0.50/1.00 | 5 |
| F | Herbicidal Compound XI | 3.00 | — | 28 |
| G | Herbicidal Compound XI/Antidotal Compound I | 3.00/1.00 | 0.33/1.00 | 27 |
| H | Herbicidal Compound VIII | 3.00 | — | 32 |
| I | Herbicidal Compound VIII/Antidotal Compound I | 3.00/1.00 | 0.33/1.00 | 28 |
| J | Herbicidal Compound X | 2.00 | — | 71 |
| K | Herbicidal Compound X/Antidotal Compound I | 2.00/1.00 | 0.50/1.00 | 63 |
| L | Herbicidal Compound VII | 0.50 | — | 100 |
| M | Herbicidal Compound VII/Antidotal Compound I | 0.50/1.00 | 2.00/1.00 | 100 |
| N | Herbicidal Compound IX | 0.0625 | — | 85 |
| O | Herbicidal Compound IX/Antidotal Compound I | 0.0625/1.00 | 16.00/1.00 | 85 |

| | |
|---|---|
| lbs. ai/A | Pounds of active ingredient per acre. |
| C | Cotton |
| S | Soybean |
| VL | Velvetleaf |
| BN | Black Nightshade |
| CG | Crabgrass |
| SI | Sida |
| P | Portulaca |
| BY | Barnyardgrass |
| SG | Sorghum Grass |
| YN | Yellow Nutsedge |
| F | Foxtail |
| MG | Morningglory |
| CO | Corn |
| European Rating System (Phototoxicity/Stand) | Visual observation of herbicidal activity rated from 1-9 as follows: 1. No Trace 2. Trace 3. Slight 4. Slight/Moderate 5. Moderate 6. Severe 7. Very Severe 8. Extremely Severe |

The results from Table I illustrate that certain composition mixtures (herbicidal compound and antidotal compound) exhibit reduced injury to cotton in preemergence incorporated applications in comparison to the injury sustained by cotton using the herbicidal compound alone (no antidotal compound). Compare the results of Examples 1 and 2 with Comparative Examples A and B respectively.

EXAMPLES 3-4 AND COMPARATIVE EXAMPLES P-BB

The response of the cotton cultivar CAMD-E, soybean, velvetleaf, black nightshade and crabgrass to the composition mixtures and compounds designated in Table II was determined for preemergence incorporated applications. Approximately 4 weeks after the preemergence incorporated applications, the herbicidal activity of the composition mixtures and compounds was determined by visual observation of the various species. These observations are reported in Table II as the standard mean of 3 replications based on a scale of 0% (no injury) to 100% (complete necrosis).

TABLE II

| Example/ Comparative Example | Treatment | Application Rate (lbs. a1/A) | Weight Ratio (Antidotal Compound/ Herbicidal Compound) | Species Injury | | | | |
|---|---|---|---|---|---|---|---|---|
| | | | | C | S | VL | BN | CG |
| 3 | Herbicidal Compound I/Antidotal Compound I | 2.00/1.00 | 0.50/1.00 | 10 | 100 | 100 | 100 | 100 |
| 4 | Herbicidal Compound II/Antidotal Compound I | 2.00/1.00 | 0.50/1.00 | 15 | 100 | 100 | 100 | 100 |
| P | Herbicidal Compound I | 2.00 | — | 100 | 100 | 100 | 100 | 18 |
| Q | Herbicidal Compound II | 2.00 | — | 100 | 100 | 100 | 100 | 100 |
| R | Antidotal Compound I | 1.00 | — | 0 | 0 | 0 | 0 | 35 |

TABLE II-continued

| Example/<br>Comparative<br>Example | Treatment | Application<br>Rate<br>(lbs. al/A) | Weight Ratio<br>(Antidotal Compound/<br>Herbicidal Compound) | Species Injury | | | | |
|---|---|---|---|---|---|---|---|---|
| | | | | C | S | VL | BN | CG |
| S | Herbicidal Compound V | 2.00 | — | 100 | 100 | 95 | 100 | 83 |
| T | Herbicidal Compound V/Antidotal Compound I | 2.00/1.00 | 0.50/1.00 | 97 | 100 | 100 | 100 | 100 |
| U | Herbicidal Compound III | 2.00 | — | 28 | 12 | 0 | 100 | 100 |
| V | Herbicidal Compound III/Antidotal Compound I | 2.00/1.00 | 0.50/1.00 | 0 | 10 | 0 | 100 | 100 |
| W | Herbicidal Compound IV | 2.00 | — | 0 | 100 | 0 | 100 | 0 |
| X | Herbicidal Compound IV/Antidotal Compound I | 2.00/1.00 | 0.50/1.00 | 0 | 100 | 0 | 100 | 72 |
| Y | Herbicidal Compound VI | 2.00 | — | 100 | 100 | 100 | 100 | 100 |
| Z | Herbicidal Compound VI/Antidotal Compound I | 2.00/1.00 | 0.50/1.00 | 100 | 100 | 100 | 100 | 100 |
| AA | Herbicidal Compound VII | 2.00 | — | 100 | 100 | 100 | 100 | 100 |
| BB | Herbicidal Compound VII/Antidotal Compound I | 2.00/1.00 | 0.50/1.00 | 100 | 100 | 100 | 100 | 100 |

The results from Table II illustrate that certain composition mixtures (herbicidal compound and antidotal compound) selectively exhibit reduced injury to cotton in preemergence incorporated applications in comparison to the injury sustained by cotton using the herbicidal compound alone (no antidotal compound). Compare the results of Examples 3 and 4 with Comparative Examples P and Q respectively.

EXAMPLES 5-16 AND COMPARATIVE EXAMPLES CC-OO

The response of the cotton cultivar CAMD-E to the composition mixtures and compounds designated in Table III was determined for preemergence incorporated applications. The weight ratio of Antidotal Compound I to Herbicidal Compound II in the composition mixtures was varied to determine a desirable weight ratio range. Approximately 4 weeks after the preemergence incorporated applications, the herbicidal activity of the composition mixtures and compounds was determined by visual observation of the cotton plants. These observations are reported in Table III as the standard mean of 3 replications based on a scale of 0% (no injury) to 100% (complete necrosis).

TABLE III

| Example/<br>Comparative<br>Example | Treatment | Application<br>Rate<br>(lbs. al/A) | Weight Ratio<br>(Antidotal Compound/<br>Herbicidal Compound) | Cotton<br>Injury |
|---|---|---|---|---|
| 5 | Herbicidal Compound II/Antidotal Compound I | 2.00/0.25 | 0.125/1.00 | 90 |
| 6 | Herbicidal Compound II/Antidotal Compound I | 2.00/0.50 | 0.25/1.00 | 90 |
| 7 | Herbicidal Compound II/Antidotal Compound I | 2.00/0.75 | 0.375/1.00 | 60 |
| 8 | Herbicidal Compound II/Antidotal Compound I | 2.00/1.00 | 0.50/1.00 | 5 |
| 9 | Herbicidal Compound II/Antidotal Compound I | 2.00/1.50 | 0.75/1.00 | 0 |
| 10 | Herbicidal Compound II/Antidotal Compound I | 2.00/2.00 | 1.00/1.00 | 0 |
| 11 | Herbicidal Compound II/Antidotal Compound I | 2.00/3.00 | 1.50/1.00 | 5 |
| 12 | Herbicidal Compound II/Antidotal Compound I | 2.00/4.00 | 2.00/1.00 | 10 |
| 13 | Herbicidal Compound II/Antidotal Compound I | 2.00/5.00 | 2.50/1.00 | 15 |
| 14 | Herbicidal Compound II/Antidotal Compound I | 2.00/6.00 | 3.00/1.00 | 15 |
| 15 | Herbicidal Compound II/Antidotal Compound I | 2.00/8.00 | 4.00/1.00 | 20 |
| 16 | Herbicidal Compound II/Antidotal Compound I | 2.00/10.00 | 5.00/1.00 | 25 |
| CC | Herbicidal Compound II | 2.00 | — | 100 |
| DD | Antidotal Compound I | 0.25 | — | 0 |
| EE | Antidotal Compound I | 0.50 | — | 0 |
| FF | Antidotal Compound I | 0.75 | — | 0 |
| GG | Antidotal Compound I | 1.00 | — | 0 |
| HH | Antidotal Compound I | 1.50 | — | 0 |
| II | Antidotal Compound I | 2.00 | — | 0 |
| JJ | Antidotal Compound I | 3.00 | — | 0 |
| KK | Antidotal Compound I | 4.00 | — | 10 |
| LL | Antidotal Compound I | 5.00 | — | 5 |
| MM | Antidotal Compound I | 6.00 | — | 15 |
| NN | Antidotal Compound I | 8.00 | — | 15 |
| OO | Antidotal Compound I | 10.00 | — | 25 |

The results from Table III illustrate that composition mixtures having a weight ratio of Antidotal Compound I to Herbicidal Compound II of from about 0.125/1.00 to about 5.00/1.00 exhibit reduced injury to cotton in preemergence incorporated applications in comparison to the injury sustained by cotton using the herbicidal compound alone (no antidotal compound).

EXAMPLES 17-24 AND COMPARATIVE EXAMPLES PP-VV

The response of the cotton cultivar CAMD-E to the composition mixtures and compounds designated in Table IV was determined for preplant incorporated applications. Approximately 4 weeks after the preplant incorporated applications, the herbicidal activity of the composition mixtures and compounds was determined by visual observation of the cotton plants. These observations are reported in Table IV as the standard mean of 3 replications based on a scale of 0% (no injury) to 100% (complete necrosis).

TABLE IV

| Example/Comparative Example | Treatment | Application Rate (lbs. a1/A) | Weight Ratio (Antidotal Compound/Herbicidal Compound) | Cotton Injury |
|---|---|---|---|---|
| 17 | Herbicidal Compound I/Antidotal Compound II | 2.00/1.00 | 0.50/1.00 | 85 |
| 18 | Herbicidal Compound I/Antidotal Compound II | 2.00/2.00 | 1.00/1.00 | 60 |
| 19 | Herbicidal Compound I/Antidotal Compound I | 2.00/1.00 | 0.50/1.00 | 75 |
| 20 | Herbicidal Compound I/Antidotal Compound I | 2.00/2.00 | 1.00/1.00 | 60 |
| 21 | Herbicidal Compound II/Antidotal Compound II | 2.00/1.00 | 0.50/1.00 | 70 |
| 22 | Herbicidal Compound II/Antidotal Compound II | 2.00/2.00 | 1.00/1.00 | 47 |
| 23 | Herbicidal Compound II/Antidotal Compound I | 2.00/1.00 | 0.50/1.00 | 72 |
| 24 | Herbicidal Compound II/Antidotal Compound I | 2.00/2.00 | 1.00/1.00 | 40 |
| PP | Herbicidal Compound I | 2.00 | — | 93 |
| QQ | Herbicidal Compound II | 2.00 | — | 87 |
| RR | Antidotal Compound II | 1.00 | — | 25 |
| SS | Antidotal Compound II | 2.00 | — | 33 |
| TT | Antidotal Compound I | 1.00 | — | 10 |
| UU | Antidotal Compound I | 2.00 | — | 20 |
| VV | None | — | — | 0 |

The results from Table IV illustrate that composition mixtures containing (i) Herbicidal Compound I and Antidotal Compound I or II and (ii) Herbicidal Compound II and Antidotal Compound I or II exhibit reduced injury to cotton in preplant incorporated applications in comparison to the injury sustained by cotton using the herbicidal compounds alone (no antidotal compound). Compare the results of Examples 17-20 with Comparative Example PP and also the results of Examples 21-24 with Comparative Example QQ.

EXAMPLES 25-32 AND COMPARATIVE EXAMPLES WW-EEE

The response of cotton cultivars (Delta Pine and Coker), sida, portulaca, barnyardgrass, sorghum grass and yellow nutsedge to the composition mixtures and compounds designated in Table V was determined for preplant incorporated applications. Approximately 4 weeks after the preplant incorporated applications, the herbicidal activity of the composition mixtures and compounds was determined by visual observation of the various species. The observations for the cotton cultivars are reported in Table V as the standard mean of 3 replications based on the European Rating system of 1-9 for phytotoxicity/stand described above. The observations for the other test species are reported in Table V as the standard mean of 3 replications based on a scale of 0% (no injury) to 100% (complete necrosis).

TABLE V

| Example/Comparative Example | Treatment | Application Rate (lbs. a1/A) | Weight Ratio (Antidotal Compound/Herbicidal Compound) | Cotton Injury | | Species Injury | | | | |
|---|---|---|---|---|---|---|---|---|---|---|
| | | | | Delta Pine | Coker | SI | P | BY | SG | YN |
| 25 | Herbicidal Compound I/Antidotal Compound II | 1.00/2.00 | 0.50/1.00 | 3/1 | 4/3 | 97 | 100 | 97 | 99 | 0 |
| 26 | Herbicidal Compound I/Antidotal Compound II | 1.00/3.00 | 3.00/1.00 | 2/1 | 2/1 | 96 | 99 | 99 | 99 | 25 |
| 27 | Herbicidal Compound I/Antidotal Compound I | 1.00/2.00 | 2.00/1.00 | 2/1 | 2/2 | 98 | 100 | 99 | 98 | 0 |
| 28 | Herbicidal Compound I/Antidotal Compound I | 1.00/3.00 | 3.00/1.00 | 1/1 | 2/1 | 92 | 97 | 95 | 95 | 3 |
| 29 | Herbicidal Compound II/Antidotal Compound II | 1.50/2.00 | 1.33/1.00 | 2/1 | 2/1 | 95 | 99 | 96 | 98 | 22 |
| 30 | Herbicidal Compound II/Antidotal Compound II | 1.50/3.00 | 3.00/1.00 | 2/1 | 2/2 | 90 | 97 | 94 | 95 | 10 |
| 31 | Herbicidal Compound II/Antidotal Compound I | 1.50/2.00 | 1.33/1.00 | 1/1 | 3/1 | 92 | 99 | 96 | 95 | 10 |
| 32 | Herbicidal Compound II/Antidotal Compound I | 1.50/3.00 | 2.00/1.00 | 1/1 | 2/1 | 97 | 100 | 98 | 98 | 17 |
| WW | Herbicidal Compound I | 1.00 | — | 5/4 | 5/5 | 94 | 99 | 95 | 98 | 0 |
| XX | Herbicidal Compound II | 1.50 | — | 3/2 | 4/3 | 97 | 96 | 97 | 95 | 0 |
| YY | Antidotal Compound II | 1.00 | — | 1/1 | 1/1 | 0 | 0 | 0 | 0 | 0 |
| ZZ | Antidotal Compound II | 2.00 | — | 1/1 | 1/1 | 0 | 0 | 0 | 0 | 0 |
| AAA | Antidotal Compound II | 3.00 | — | 1/1 | 1/1 | 42 | 62 | 55 | 52 | 13 |
| BBB | Antidotal Compound I | 1.00 | — | 1/1 | 1/1 | 0 | 0 | 0 | 0 | 0 |
| CCC | Antidotal Compound I | 2.00 | — | 1/1 | 1/1 | 0 | 0 | 0 | 0 | 0 |
| DDD | Antidotal Compound I | 3.00 | — | 1/1 | 1/1 | 27 | 56 | 47 | 43 | 30 |
| EEE | None | — | — | 1/1 | 1/1 | 0 | 0 | 0 | 0 | 0 |

The results from Table V illustrate that composition mixtures containing (i) Herbicidal Compound I and Antidotal Compound I or II and (ii) Herbicidal Compound II and Antidotal Compound I or II selectively exhibit reduced injury to cotton in preplant incorporated applications in comparison to the injury sustained by cotton using the herbicidal compounds alone (no antidotal compound). Compare the results of Examples 25-28 with Comparative Example WW and also the results of Examples 29-32 with Comparative Example XX.

EXAMPLES 33-40 AND COMPARATIVE EXAMPLES FFF-JJJ

The response of various cotton cultivars to the composition mixtures and compounds designated in Table VI was determined for preemergence applications with or without a preplant incorporated application. In particular, for Examples 33–40, a preplant incorporated application of either Antidotal Compound I or II was followed by a preemergence application of either Herbicidal Compound I or II. Comparative examples FFF and GGG had only a preemergence application of Herbicidal Compound I and II respectively. Comparative Examples III and JJJ had only a preplant incorporated application of Antidotal Compound II and I respectively. Approximately 6 weeks after the specified applications, the herbicidal activity of the composition mixtures and compounds was determined by visual observation of the various cotton plants. These observations are reported in Table VI as the standard means of 3 replications based on a scale of 0% (no injury) to 100% (complete necrosis).

Table VII was determined for preemergence applications. Approximately 4 weeks after the preemergence applications, the herbicidal activity of the composition mixtures and compounds was determined by visual observation of the cotton plants. These observations are reported in Table VII as the standard mean of 3 replications based on a scale of 0% (no injury) to 100% (complete necrosis).

TABLE VII

| Example/ Comparative Example | Treatment | Application Rate (lbs. a1/A) | Weight Ratio (Antidotal Compound/ Herbicidal Compound) | Cotton Injury |
|---|---|---|---|---|
| 41 | Herbicidal Compound II/Antidotal Compound II | 1.00/1.00 | 1.00/1.00 | 20 |
| 42 | Herbicidal Compound II/Antidotal Compound II | 2.00/1.00 | 0.50/1.00 | 40 |
| 43 | Herbicidal Compound II/Antidotal Compound I | 1.00/1.00 | 1.00/1.00 | 0 |
| 44 | Herbicidal Compound II/Antidotal Compound I | 2.00/1.00 | 0.50/1.00 | 43 |
| KKK | Herbicidal Compound II | 1.00 | — | 60 |
| LLL | Herbicidal Compound II | 2.00 | — | 100 |
| MMM | Antidotal Compound II | 1.00 | — | 0 |
| NNN | Antidotal Compound I | 1.00 | — | 0 |

The results from Table VII illustrate that composition mixtures containing Herbicidal Compound II and either Antidotal Compound I or II exhibit reduced injury to cotton in preemergence applications in comparison to the injury sustained by cotton using the herbicidal compound alone (no antidotal compound). Compare the results of Examples 41 and 43 with Com-

TABLE VI

| Example/ Comparative Example | Treatment | Application Rate (lbs. a1/A) | Weight Ratio (Antidotal Compound/ Herbicidal Compound) | Cotton Injury | | | |
|---|---|---|---|---|---|---|---|
| | | | | Stoneville 213 | Stoneville 825 | Delta Pine 41 | Delta Pine 61 |
| 33 | Herbicidal Compound I/Antidotal Compound II | 1.00/2.00 | 2.00/1.00 | 70 | 30 | 43 | 37 |
| 34 | Herbicidal Compound I/Antidotal Compound II | 1.00/3.00 | 3.00/1.00 | 90 | 53 | 57 | 47 |
| 35 | Herbicidal Compound I/Antidotal Compound I | 1.00/2.00 | 2.00/1.00 | 79 | 40 | 60 | 63 |
| 36 | Herbicidal Compound I/Antidotal Compound I | 1.00/3.00 | 3.00/1.00 | 78 | 47 | 60 | 73 |
| 37 | Herbicidal Compound II/Antidotal Compound II | 1.50/2.00 | 1.33/1.00 | 92 | 60 | 70 | 67 |
| 38 | Herbicidal Compound II/Antidotal Compound II | 1.50/3.00 | 2.00/1.00 | 88 | 67 | 73 | 70 |
| 39 | Herbicidal Compound II/Antidotal Compound I | 1.50/2.00 | 1.33/1.00 | 70 | 33 | 63 | 60 |
| 40 | Herbicidal Compound II/Antidotal Compound I | 1.50/3.00 | 2.00/1.00 | 70 | 37 | 50 | 53 |
| FFF | Herbicidal Compound I | 1.00 | — | 98 | 85 | 93 | 77 |
| GGG | Herbicidal Compound II | 1.50 | — | 95 | 88 | 93 | 72 |
| HHH | None | — | — | 0 | 0 | 0 | 0 |
| III | Antidotal Compound II | 3.00 | — | 20 | 17 | 20 | 27 |
| JJJ | Antidotal Compound I | 3.00 | — | 17 | 7 | 17 | 13 |

The results from Table VI illustrate that cotton cultivars exposed to both an antidotal compound preplant incorporated application and herbicidal compound preemergence application exhibit reduced injury in comparison to the injury sustained by the cotton cultivars using only a preemergence application of herbicidal compound alone (no antidotal compound). Compare the results of Examples 33–36 with Comparative Example FFF and also the results of Examples 37–40 with Comparative Example GGG.

EXAMPLES 41–44 AND COMPARATIVE EXAMPLES KKK–NNN

The response of cotton cultivar CAMD-E to the composition mixtures and compounds designated in parative Example KKK and also the results of Examples 42 and 44 with Comparative Example LLL.

EXAMPLES 45–48 AND COMPARATIVE EXAMPLES OOO–RRR

The response of cotton cultivar Delta Pine 41 to the composition mixtures and compounds designated in Table VIII was determined for preemergence applications. Approximately 4 weeks after the preemergence applications, the herbicidal activity of the composition mixtures and compounds was determined by visual observation of the cotton plants. These observations are reported in Table VIII as the standard mean of 3 replications based on a scale of 0% (no injury) to 100% (complete necrosis).

TABLE VIII

| Example/ Comparative Example | Treatment | Application Rate (lbs. a1/A) | Weight Ratio (Antidotal Compound/ Herbicidal Compound) | Cotton Injury |
|---|---|---|---|---|
| 45 | Herbicidal Compound I/Antidotal Compound II | 2.00/2.00 | 1.00/1.00 | 62 |
| 46 | Herbicidal Compound I/Antidotal Compound I | 2.00/2.00 | 1.00/1.00 | 67 |
| 47 | Herbicidal Compound II/Antidotal Compound II | 2.00/2.00 | 1.00/1.00 | 50 |

TABLE VIII-continued

| Example/Comparative Example | Treatment | Application Rate (lbs. a1/A) | Weight Ratio (Antidotal Compound/ Herbicidal Compound) | Cotton Injury |
|---|---|---|---|---|
| 48 | Herbicidal Compound II/Antidotal Compound I | 2.00/2.00 | 1.00/1.00 | 43 |
| OOO | Herbicidal Compound I | 2.00 | — | 90 |
| PPP | Herbicidal Compound II | 2.00 | — | 85 |
| QQQ | Antidotal Compound II | 2.00 | — | 38 |
| RRR | Antidotal Compound I | 2.00 | — | 30 |

The results from Table VIII illustrate that composition mixtures containing (i) Herbicidal Compound I and Antidotal Compound I or II and (ii) Herbicidal Compound II and Antidotal Compound I or II exhibit reduced injury to cotton in preemergence applications in comparison to the injury sustained by cotton using the herbicidal compound alone (no antidotal compound). Compare the results of Examples 45 and 46 with Comparative Example OOO and also the results of Examples 47 and 48 with Comparative Example PPP.

EXAMPLES 49–56 AND COMPARATIVE EXAMPLES SSS–WWW

The response of various cotton cultivars to the composition mixtures and compounds designated in Table IX was determined for preemergence applications. Approximately 6 weeks after the preemergence applications, the herbicidal activity of the composition mixtures and compounds was determined by visual observation of the cotton plants. These observations are reported in Table IX as the standard means of 3 replications based on a scale of 0% (no injury) to 100% (complete necrosis).

The results from Table IX illustrate that composition mixtures containing (i) Herbicidal Compound I and Antidotal Compound I or II and (ii) Herbicidal Compound II and Antidotal Compound I or II exhibit reduced injury to the cotton cultivars in preemergence applications in comparison to the injury sustained by the cotton cultivars using the herbicidal compound alone (no antidotal compound). Compare the results of Examples 49–52 with Comparative Example SSS and also the results of Examples 53–56 with Comparative Example TTT.

EXAMPLES 57–64 AND COMPARATIVE EXAMPLES XXX–FFFF

The response of cotton cultivars (Delta Pine and Coker), sida, portulaca, barnyardgrass, sorghum grass and yellow nutsedge to the composition mixtures and compounds designated in Table X was determined for preemergence applications. Approximately 4 weeks after the preemergence applications, the herbicidal activity of the composition mixtures and compounds was determined by visual observation of the various species. The observations for the cotton cultivars are reported in Table X as the standard mean of 3 replications based on the European Rating System of 1–9 for phytotoxicity/stand described above. The observations for the other test species are reported in Table X as the standard mean of 3 replications based on a scale of 0% (no injury) to 100% (complete necrosis).

TABLE IX

| Example/Comparative Example | Treatment | Application Rate (lbs. a1/A) | Weight Ratio (Antidotal Compound/ Herbicidal Compound) | Cotton Injury | | | |
|---|---|---|---|---|---|---|---|
| | | | | Stoneville 213 | Stoneville 825 | Delta Pine 41 | Delta Pine 61 |
| 49 | Herbicidal Compound I/Antidotal Compound II | 1.00/2.00 | 2.00/1.00 | 93 | 80 | 88 | 88 |
| 50 | Herbicidal Compound I/Antidotal Compound II | 1.00/3.00 | 3.00/1.00 | 88 | 63 | 77 | 77 |
| 51 | Herbicidal Compound I/Antidotal Compound I | 1.00/2.00 | 2.00/1.00 | 90 | 67 | 95 | 85 |
| 52 | Herbicidal Compound I/Antidotal Compound I | 1.00/3.00 | 3.00/1.00 | 87 | 63 | 93 | 88 |
| 53 | Herbicidal Compound II/Antidotal Compound II | 1.50/2.00 | 1.33/1.00 | 73 | 20 | 60 | 30 |
| 54 | Herbicidal Compound II/Antidotal Compound II | 1.50/3.00 | 2.00/1.00 | 72 | 30 | 47 | 60 |
| 55 | Herbicidal Compound II/Antidotal Compound I | 1.50/2.00 | 1.33/1.00 | 60 | 20 | 50 | 47 |
| 56 | Herbicidal Compound II/Antidotal Compound I | 1.50/3.00 | 2.00/1.00 | 60 | 33 | 50 | 53 |
| SSS | Herbicidal Compound I | 1.00 | — | 98 | 85 | 93 | 97 |
| TTT | Herbicidal Compound II | 1.50 | — | 95 | 88 | 93 | 72 |
| UUU | None | — | — | 0 | 0 | 0 | 0 |
| VVV | Antidotal Compound II | 3.00 | — | 7 | 0 | 0 | 7 |
| WWW | Antidotal Compound I | 3.00 | — | 0 | 0 | 0 | 0 |

TABLE X

| Example/Comparative Example | Treatment | Application Rate (lbs. a1/A) | Weight Ratio (Antidotal Compound/ Herbicidal Compound) | Cotton Injury | | Species Injury | | | | |
|---|---|---|---|---|---|---|---|---|---|---|
| | | | | Delta Pine | Coker | SI | P | BY | SG | YN |
| 57 | Herbicidal Compound I/Antidotal Compound II | 1.00/2.00 | 2.00/1.00 | 3/3 | 4/3 | 99 | 100 | 100 | 100 | 47 |
| 58 | Herbicidal Compound I/Antidotal Compound II | 1.00/3.00 | 3.00/1.00 | 2/1 | 3/2 | 98 | 100 | 100 | 98 | 47 |
| 59 | Herbicidal Compound I/Antidotal Compound I | 1.00/2.00 | 2.00/1.00 | 2/1 | 3/1 | 96 | 100 | 99 | 99 | 10 |
| 60 | Herbicidal Compound I/Antidotal Compound I | 1.00/3.00 | 3.00/1.00 | 1/1 | 2/1 | 97 | 100 | 100 | 98 | 70 |
| 61 | Herbicidal Compound II/Antidotal Compound II | 1.50/2.00 | 1.33/1.00 | 2/1 | 3/1 | 99 | 100 | 100 | 100 | 54 |
| 62 | Herbicidal Compound II/Antidotal | 1.50/3.00 | 2.00/1.00 | 2/1 | 3/1 | 90 | 100 | 100 | 100 | 70 |

TABLE X-continued

| Example/<br>Comparative<br>Example | Treatment | Application<br>Rate<br>(lbs. a1/A) | Weight Ratio<br>(Antidotal Compound/<br>Herbicidal Compound) | Cotton Injury | | Species Injury | | | | |
|---|---|---|---|---|---|---|---|---|---|---|
| | | | | Delta Pine | Coker | SI | P | BY | SG | YN |
| | Compound II | | | | | | | | | |
| 63 | Herbicidal Compound II/Antidotal Compound I | 1.50/2.00 | 1.33/1.00 | 3/1 | 3/1 | 100 | 100 | 100 | 100 | 22 |
| 64 | Herbicidal Compound II/Antidotal Compound I | 1.50/3.00 | 2.00/1.00 | 1/1 | 2/1 | 100 | 100 | 100 | 100 | 72 |
| XXX | Herbicidal Compound I | 1.00 | — | 5/4 | 6/5 | 98 | 100 | 98 | 90 | 0 |
| YYY | Herbicidal Compound II | 1.50 | — | 5/2 | 5/3 | 96 | 100 | 100 | 99 | 0 |
| ZZZ | Antidotal Compound II | 1.00 | — | 1/1 | 1/1 | 0 | 0 | 0 | 0 | |
| AAAA | Antidotal Compound II | 2.00 | — | 1/1 | 1/1 | 0 | 0 | 0 | 0 | 0 |
| BBBB | Antidotal Compound II | 3.00 | — | 1/1 | 1/1 | 0 | 25 | 40 | 45 | 0 |
| CCCC | Antidotal Compound I | 1.00 | — | 1/1 | 1/1 | 0 | 0 | 17 | 38 | 0 |
| DDDD | Antidotal Compound I | 2.00 | — | 1/1 | 1/1 | 0 | 0 | 45 | 32 | 65 |
| EEEE | Antidotal Compound I | 3.00 | — | 1/1 | 1/1 | 0 | 20 | 82 | 82 | 40 |
| FFFF | None | — | — | 1/1 | 1/1 | 0 | 0 | 0 | 0 | 0 |

The results from Table X illustrate that composition mixtures containing (i) Herbicidal Compound I and Antidotal Compound I or II and (ii) Herbicidal Compound II and Antidotal Compound I or II selectively exhibit reduced injury to cotton in preemergence applications in comparison to the injury sustained by cotton using the herbicidal compound alone (no antidotal compound). Compare the results of Examples 57–60 with Comparative Example XXX and also the results of Examples 61–64 with Comparative Examples YYY.

EXAMPLES 65–76 AND COMPARATIVE EXAMPLES GGGG–OOOO

The response of cotton cultivars (Delta Pine and Coker) to the composition mixtures and compounds designated in Table XI was determined for preemergence applications with or without a seed application. In particular, for Examples 65–76, a seed application of either Antidotal Compound I or II was followed by a preemergence application of either Herbicidal Compound I or II. Comparative Examples GGGG and HHHH did not have a seed application. Approximately 4 weeks after the specified applications, the herbicidal activity of the composition mixtures and compounds was determined by visual observation of the cotton cultivars. The observations for the cotton cultivars are reported in Table XI as the standard mean of 3 replications based on the European Rating System of 1–9 for phytotoxicity/stand described above.

TABLE XI

| Example/<br>Comparative<br>Example | Treatment | Herbicidal Compound<br>Application Rate<br>(lbs. a1/A) | Antidotal Compound<br>Solution Concentration<br>(%) | Cotton Injury | |
|---|---|---|---|---|---|
| | | | | Delta Pine | Coker |
| 65 | Herbicidal Compound I/Antidotal Compound II | 2.00 | 0.50 | 6/5 | 6/5 |
| 66 | Herbicidal Compound I/Antidotal Compound II | 2.00 | 5.00 | 3/3 | 3/3 |
| 67 | Herbicidal Compound I/Antidotal Compound II | 2.00 | 10.00 | 2/2 | 2/2 |
| 68 | Herbicidal Compound I/Antidotal Compound I | 2.00 | 0.50 | 6/6 | 6/6 |
| 69 | Herbicidal Compound I/Antidotal Compound I | 2.00 | 5.00 | 3/3 | 3/3 |
| 70 | Herbicidal Compound I/Antidotal Compound I | 2.00 | 10.00 | 3/2 | 2/2 |
| 71 | Herbicidal Compound II/Antidotal Compound II | 2.00 | 0.50 | 1/1 | 1/1 |
| 72 | Herbicidal Compound II/Antidotal Compound II | 2.00 | 5.00 | 1/1 | 1/1 |
| 73 | Herbicidal Compound II/Antidotal Compound II | 2.00 | 10.00 | 1/1 | 1/1 |
| 74 | Herbicidal Compound II/Antidotal Compound I | 2.00 | 0.50 | 1/1 | 1/1 |
| 75 | Herbicidal Compound II/Antidotal Compound I | 2.00 | 5.00 | 1/1 | 1/1 |
| 76 | Herbicidal Compound II/Antidotal Compound I | 2.00 | 10.00 | 1/1 | 1/1 |
| GGGG | Herbicidal Compound I | 2.00 | — | 7/8 | 8/8 |
| HHHH | Herbicidal Compound II | 2.00 | — | 2/1 | 2/1 |
| IIII | None | — | — | 1/1 | 1/1 |
| JJJJ | None | — | — | 1/1 | 1/1 |
| KKKK | None | — | — | 1/1 | 1/1 |
| LLLL | None | — | — | 1/1 | 1/1 |
| MMMM | None | — | — | 1/1 | 1/1 |
| NNNN | None | — | — | 1/1 | 1/1 |
| OOOO | None | — | — | 1/1 | 1/1 |

The results from Table XI illustrate that the cotton cultivars exposed to both an antidotal compound seed application and herbicidal compound preemergence application exhibit reduced injury in comparison to the injury sustained by the cotton cultivars using only a preemergence application of the herbicidal compound alone (no antidotal compound). Compare the results of Examples 65–70 with Comparative Example GGGG and also the results of Examples 71–76 with Comparative Example HHHH.

EXAMPLES 77–88 AND COMPARATIVE EXAMPLES PPPP–XXXX

The response of cotton cultivar Delta Pine 41 to the composition mixtures and compounds designated in Table XII was determined for preemergence applications with or without a seed application. In particular, for examples 77–88, a seed application of either Antidotal Compound I or II was followed by a preemergence application of either Herbicidal Compound I or II. Comparative Examples PPPP and QQQQ did not have a seed application. Approximately 4 weeks after the specified applications, the herbicidal activity of the composition mixtures and compounds was determined by visual observation of the cotton cultivar. The observations for the cotton cultivar are reported in Table XII as the standard mean of 3 replications based on a scale of 0% (no injury) to 100% (complete necrosis).

the herbicidal activity of the composition mixtures and compounds was determined by visual observation of the various test species. These observations are reported in

TABLE XII

| Example/ Comparative Example | Treatment | Herbicidal Compound Application Rate (lbs. a1/A) | Antidotal Compound Solution Concentration (%) | Cotton Injury |
|---|---|---|---|---|
| 77 | Herbicidal Compound II/Antidotal Compound II | 2.00 | 1.00 | 73 |
| 78 | Herbicidal Compound II/Antidotal Compound II | 2.00 | 5.00 | 65 |
| 79 | Herbicidal Compound II/Antidotal Compound II | 2.00 | 10.00 | 70 |
| 80 | Herbicidal Compound II/Antidotal Compound I | 2.00 | 1.00 | 73 |
| 81 | Herbicidal Compound II/Antidotal Compound I | 2.00 | 5.00 | 62 |
| 82 | Herbicidal Compound II/Antidotal Compound I | 2.00 | 10.00 | 72 |
| 83 | Herbicidal Compound I/Antidotal Compound II | 2.00 | 1.00 | 92 |
| 84 | Herbicidal Compound I/Antidotal Compound II | 2.00 | 5.00 | 97 |
| 85 | Herbicidal Compound I/Antidotal Compound II | 2.00 | 10.00 | 90 |
| 86 | Herbicidal Compound I/Antidotal Compound I | 2.00 | 1.00 | 97 |
| 87 | Herbicidal Compound I/Antidotal Compound I | 2.00 | 5.00 | 93 |
| 88 | Herbicidal Compound I/Antidotal Compound I | 2.00 | 10.00 | 97 |
| PPPP | Herbicidal Compound II | 2.00 | — | 85 |
| QQQQ | Herbicidal Compound I | 2.00 | — | 98 |
| RRRR | None | — | — | 0 |
| SSSS | Antidotal Compound II | — | 1.00 | 0 |
| TTTT | Antidotal Compound II | — | 5.00 | 0 |
| UUUU | Antidotal Compound II | — | 10.00 | 0 |
| VVVV | Antidotal Compound I | — | 1.00 | 0 |
| WWWW | Antidotal Compound I | — | 5.00 | 0 |
| XXXX | Antidotal Compound I | — | 10.00 | 0 |

The results from Table XII illustrate that the cotton cultivar exposed to both an antidotal compound seed application and herbicidal compound preemergence Table XIII as the standard mean of 3 replications based on a scale of 0% (no injury) to 100% (complete necrosis).

TABLE XIII

| Example/ Comparative Example | Treatment | Application Rate (lbs. a1/A) | Weight Ratio (Antidotal Compound/ Herbicidal Compound) | Species Injury | | | | | | |
|---|---|---|---|---|---|---|---|---|---|---|
| | | | | C | S | F | CG | VL | MG | CO |
| YYYY | Herbicidal Compound I/Antidotal Compound II | 2.00/0.50 | 0.25/1.00 | 100 | 100 | 40 | 35 | 100 | 100 | 0 |
| ZZZZ | Herbicidal Compound I/Antidotal Compound II | 2.00/1.00 | 0.50/1.00 | 100 | 100 | 90 | 75 | 100 | 100 | 0 |
| AAAAA | Herbicidal Compound I/Antidotal Compound I | 2.00/0.50 | 0.25/1.00 | 100 | 100 | 35 | 30 | 100 | 100 | 0 |
| BBBBB | Herbicidal Compound I/Antidotal Compound I | 2.00/1.00 | 0.50/1.00 | 100 | 100 | 50 | 65 | 100 | 100 | 0 |
| CCCCC | Herbicidal Compound II/Antidotal Compound II | 2.00/0.50 | 0.25/1.00 | 100 | 100 | 100 | 95 | 100 | 100 | 0 |
| DDDDD | Herbicidal Compound II/Antidotal Compound II | 2.00/1.00 | 0.50/1.00 | 100 | 100 | 100 | 98 | 100 | 100 | 0 |
| EEEEE | Herbicidal Compound II/Antidotal Compound I | 2.00/0.50 | 0.25/1.00 | 100 | 30 | 40 | 95 | 100 | 100 | 0 |
| FFFFF | Herbicidal Compound II/Antidotal Compound I | 2.00/1.00 | 0.50/1.00 | 100 | 25 | 40 | 90 | 100 | 100 | 0 |
| GGGGG | Herbicidal Compound I | 2.00 | — | 100 | 100 | 95 | 75 | 100 | 100 | 0 |
| HHHHH | Herbicidal Compound II | 2.00 | — | 100 | 100 | 100 | 100 | 100 | 100 | 0 |
| IIIII | Antidotal Compound II | 0.50 | — | 0 | 0 | 0 | 0 | 0 | 0 | 0 |
| JJJJJ | Antidotal Compound II | 1.00 | — | 0 | 0 | 0 | 0 | 0 | 0 | 0 |
| KKKKK | Antidotal Compound I | 0.50 | — | 0 | 0 | 15 | 0 | 0 | 0 | 0 |
| LLLLL | Antidotal Compound I | 1.00 | — | 0 | 0 | 15 | 10 | 0 | 0 | 0 | application exhibits reduced injury in comparison to the injury sustained by the cotton cultivar using only a preemergence application of the herbicidal compound alone (no antidotal compound). Compare the results of Examples 77-82 with Comparative Example PPPP and also the results of Examples 83-88 with Comparative Example QQQQ.

COMPARATIVE EXAMPLES YYYY-LLLLL

The response of the cotton cultivar CAMD-E, soybean, foxtail, crabgrass, velvetleaf, morningglory and corn to the composition mixtures and compounds designated in Table XIII was determined for postemergence applications. The treatments were applied when the various test species were at the 1-2 leaf stage. Approximately 2 weeks after the post emergence applications, The results from Table XIII illustrate that no effect is observed when composition mixtures containing (i) Hericidal Compound I and Antidotal Compound I or II and (ii) Herbicidal Compound II and Antidotal Compound I or II are applied postemergence.

We claim:

1. A herbicidal composition for selective control of undesirable vegation in cotton crops comprising (i) a herbicidally effective amount of a herbicidal compound selected from 2-chloro-4-(ethylamino)-6-(isopropylamino)-S-triazine and 2-chloro-4-(1-cyano-1-methylethylamino)-6-ethylamino-S-triazine and (ii) an antidotally effective amount of an antidotal compound selected from 1-(alpha, alpha-dimethylbenzyl)-3-methyl 3-phenyl urea and 1-(alpha, alpha-dimethylbenzyl)-3-methoxy-3-phenyl urea.

2. The herbicidal composition of claim 1 wherein the herbicidal compound is 2-chloro-4-(ethylamino)-6-(isopropylamino)-S-triazine and the antidotal compound is 1-(alpha, alpha-dimethylbenzyl)-3-methyl-3-phenyl urea.

3. The herbicidal composition of claim 1 wherein the herbicidal compound is 2-chloro-4-(ethylamino)-6-(isopropylamino)-S-triazine and the antidotal compound is 1-(alpha, alpha-dimethylbenzyl)-3-methoxy-3-phenyl urea.

4. The herbicidal composition of claim 1 wherein the herbicidal compound is 2-chloro-4-(1-cyano-1-methylethylamino)-6-ethylamino-S-triazine and the antidotal compound is 1-(alpha, alpha-dimethylbenzyl)-3-methyl-3-phenyl urea.

5. The herbicidal composition of claim 1 wherein the herbicidal compound is 2-chloro-4-(1-cyano-1-methylethylamino)-6-ethylamino-S-triazine and the antidotal compound is 1-(alpha, alpha-dimethylbenzyl)-3-methoxy-3-phenyl urea.

6. A method of protecting cotton plants from injury due to a herbicidal compound selected from 2-chloro-4-(ethylamino)-6-(isopropylamino)-S-triazine and 2-chloro-4-(1-cyano-1-methylethylamino)-6-ethylamino-S-triazine which comprises combining application of a herbicidally effective amount of said herbicidal compound to the locus to be treated with application of an antidotally effective amount of an antidotal compound selected from 1-(alpha, alpha-dimethylbenzyl)-3-methyl-3-phenyl urea and 1-(alpha, alpha-dimethylbenzyl)-3-methoxy-3-phenyl urea.

7. The method of claim 6 wherein said herbicidal compound and antidotal compound are applied to the soil in which cotton seeds have been planted prior to emergence of the cotton seeds.

8. The method of claim 6 wherein said herbicidal compound and antidotal compound are applied to the soil and incorporated in the soil prior to the planting of the cotton seeds.

9. The method of claim 6 wherein cotton seeds are coated with said antidotal compound prior to planting.

10. The method of claim 9 wherein said herbicidal compound is applied to the soil in which the coated cotton seeds have been planted prior to emergence of the coated cotton seeds.

11. The method of claim 6 wherein said antidotal compound is applied to the soil in which cotton seeds are to be planted.

12. The method of claim 11 wherein said herbicidal compound is applied to the treated soil in which the cotton seeds have been planted prior to emergence of the cotton seeds.

* * * * *